US009002439B2

(12) United States Patent
Okada et al.

(10) Patent No.: US 9,002,439 B2
(45) Date of Patent: Apr. 7, 2015

(54) BLOOD VESSEL WALL ANALYZING DEVICE AND BLOOD VESSEL WALL ANALYZING METHOD

(75) Inventors: Kazunori Okada, Yokohama (JP); Hiroshi Suganuma, Yokohama (JP); Tatsuhiko Saito, Yokohama (JP); Masato Tanaka, Yokohama (JP); Akira Ishii, Kyoto (JP); Toshihiro Munemitsu, Kyoto (JP); Eiji Okada, Yokohama (JP)

(73) Assignees: Sumitomo Electric Industries, Ltd., Osaka-shi (JP); Kyoto University, Kyoto-shi (JP); Keio University, Tokyo (JP)

( * ) Notice: Subject to any disclaimer, the term of this patent is extended or adjusted under 35 U.S.C. 154(b) by 522 days.

(21) Appl. No.: 13/320,005

(22) PCT Filed: May 13, 2010

(86) PCT No.: PCT/JP2010/058085
§ 371 (c)(1),
(2), (4) Date: Jan. 11, 2012

(87) PCT Pub. No.: WO2010/131697
PCT Pub. Date: Nov. 18, 2010

(65) Prior Publication Data
US 2012/0101391 A1    Apr. 26, 2012

(30) Foreign Application Priority Data
May 13, 2009    (JP) .................................. 2009-116792

(51) Int. Cl.
*A61B 6/00*    (2006.01)
*A61B 5/02*    (2006.01)
(Continued)

(52) U.S. Cl.
CPC ........... *A61B 5/02007* (2013.01); *A61B 5/0075* (2013.01); *A61B 5/0086* (2013.01); *A61B 5/7425* (2013.01); *A61B 5/743* (2013.01); *A61B 5/0062* (2013.01); *G01N 21/359* (2013.01)

(58) Field of Classification Search
None
See application file for complete search history.

(56) References Cited

U.S. PATENT DOCUMENTS

| 5,197,470 A | 3/1993 | Helfer et al. |
| 5,441,053 A | 8/1995 | Lodder et al. |

(Continued)

FOREIGN PATENT DOCUMENTS

| CN | 1744853 A | 3/2006 |
| CN | 1878504 A | 12/2006 |

(Continued)

OTHER PUBLICATIONS

Prabhudesai et al., "The Potential Role of Optical Coherence Tomography in the Evaluation of Vulnerable Carotid Atheromatous Plaques: A Pilot Study", Cardiovasc. Intervent Radiol., Sep. 2006, pp. 1039-1045.*

(Continued)

*Primary Examiner* — Christopher Cook
(74) *Attorney, Agent, or Firm* — Venable LLP; Steven J. Schwarz; George L. Howarah

(57) ABSTRACT

The present invention relates to a blood vessel wall analyzing apparatus provided with a structure enabling accurate measurement of plaque components in a blood vessel wall in a state that reduces the burden on a patient. In the blood vessel wall analyzing apparatus (1), measurement light is illuminated onto a measured portion within a blood vessel such as a carotid artery (C) from a light illuminating unit (30) provided outside the blood vessel, while light from the measured portion is detected in a light receiving unit (40) provided outside the blood vessel. Thus, since the status of the blood vessel wall can be analyzed without inserting an apparatus involved in measurement into the blood vessel, the burden on the patient is reduced during measurement. In addition, as a result of carrying out measurement using near infrared light (a light component in the wavelength range of 780 nm to 2750 nm) that exhibits characteristics that differ according to the compositions of substances such as plaque adhered within the blood vessel, analysis can be carried out that distinguish compositions such as plaque using an analyzing apparatus provided outside the blood vessel.

6 Claims, 13 Drawing Sheets

(51) Int. Cl.
   *A61B 5/00* (2006.01)
   *G01N 21/359* (2014.01)

(56) References Cited

U.S. PATENT DOCUMENTS

| | | | |
|---|---|---|---|
| 7,539,530 | B2 | 5/2009 | Caplan et al. |
| 2003/0191378 | A1 | 10/2003 | Davis et al. |
| 2004/0024298 | A1 | 2/2004 | Marshik-Geurts et al. |
| 2004/0024321 | A1 | 2/2004 | Marshik-Geurts et al. |
| 2004/0077950 | A1 | 4/2004 | Marshik-Geurts et al. |
| 2005/0043637 | A1 | 2/2005 | Caplan et al. |
| 2005/0228295 | A1 | 10/2005 | Tan |
| 2008/0221455 | A1 | 9/2008 | Marshik-Geurts et al. |
| 2008/0300493 | A1 | 12/2008 | Gatto et al. |
| 2010/0160749 | A1* | 6/2010 | Gross et al. .......... 600/316 |

FOREIGN PATENT DOCUMENTS

| | | |
|---|---|---|
| CN | 102056534 A | 5/2011 |
| JP | 2004-329550 | 11/2004 |
| JP | 2005-287964 | 10/2005 |
| JP | 2005-534415 | 11/2005 |
| JP | 2005-534428 | 11/2005 |
| JP | 2007-503224 | 2/2007 |
| JP | 2007-185242 | 7/2007 |
| JP | 2007-531598 | 11/2007 |
| JP | 2008-229156 | 10/2008 |
| JP | 2008-259743 | 10/2008 |
| JP | 2009-028013 | 2/2009 |
| RU | 2 168 927 C2 | 6/2001 |
| WO | WO-2006/020292 A2 | 2/2006 |

OTHER PUBLICATIONS

Farooq et al., "The role of opticl coherence tomography in vascular medicine", Vascular Medicine, Jan. 14, 2009, pp. 63-71.*
International Search Report in International Application No. PCT/JP2010/058119 dated Jun. 8, 2010.
International Preliminary Report on Patentability and Written Opinion in International Application No. PCT/JP2010/058119 dated Dec. 22, 2011.
Office Action in Chinese Patent Application No. 201080021100.2, dated Jan. 3, 2014.
Office Action issued in Chinese Patent Application No. 201080021077.7 dated May 31, 2013.
Extended European Search Report in European Patent Application No. 10774970.7, dated Nov. 20, 2013.
Xia et al., "Mid-infrared supercontinuum generation to 4.5 µm in ZBLAN fluoride fibers by nanosecond diode pumping," Optics Letters, vol. 31, No. 17, pp. 2553-2555, (Sep. 1, 2006).
Office Action issued in U.S. Appl. No. 13/319,976 dated Jan. 9, 2013.
Notice of Allowance in Russian Patent Application No. 2011150502, dated Jun. 9, 2014.
Extended European Search Report in European Patent Application No. 10774954.1, dated Jan. 12, 2015.

* cited by examiner

Fig.3
(A)
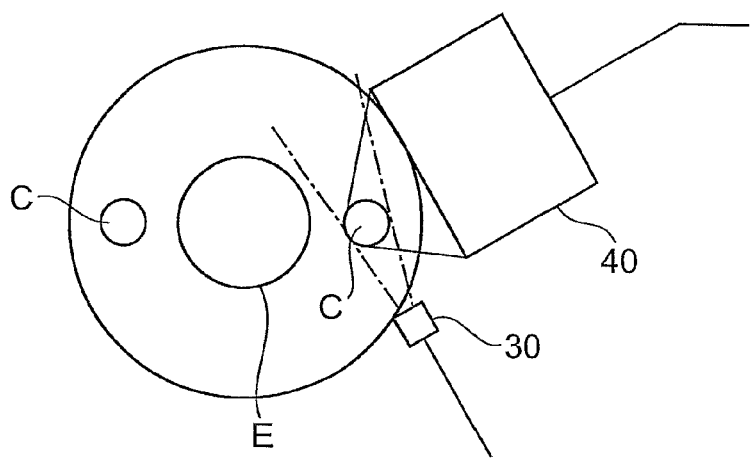
(B)
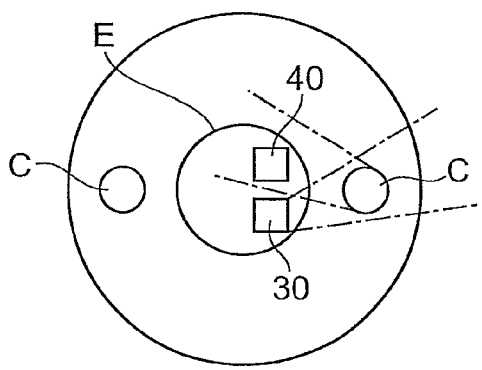

Fig.12
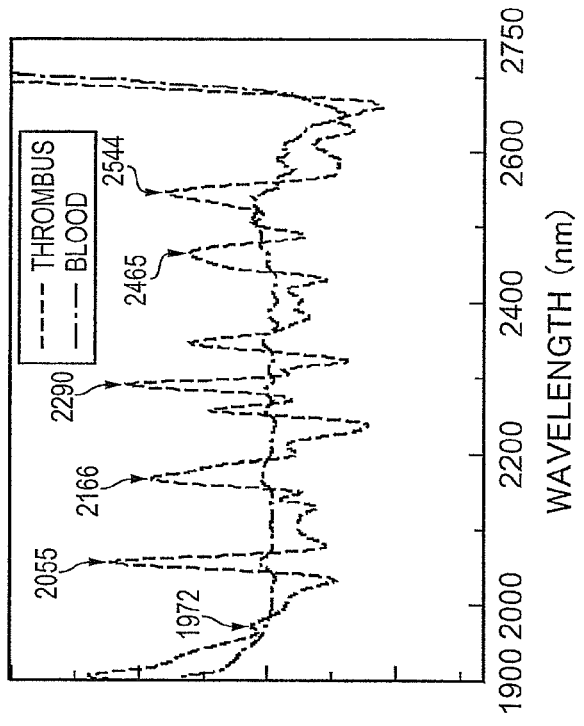
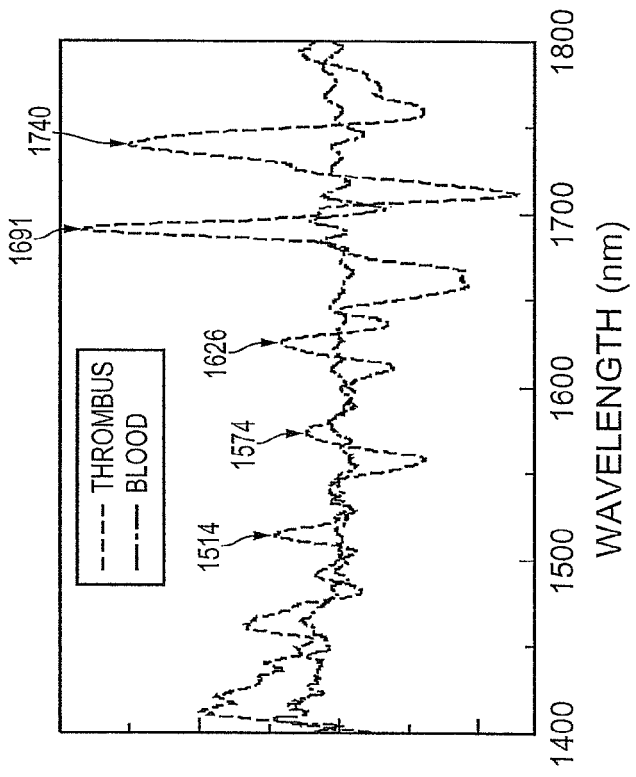

BLOOD VESSEL WALL ANALYZING DEVICE AND BLOOD VESSEL WALL ANALYZING METHOD

TECHNICAL FIELD

The present invention relates to a blood vessel wall analyzing apparatus suitable for analyzing compositions of a measured portion within a blood vessel, and to a blood vessel wall analyzing method.

BACKGROUND ART

Carotid artery plaque is known to be an important factor that induces cerebral infarction. Carotid artery plaque is an attached substance that is formed on the inner walls of the carotid arteries by blood cholesterol, neutral fats and the like. In the case this attached substance separates from an inner wall of a carotid artery and obstructs a portion of an intracerebral blood vessel, it can cause a serious disorder such as cerebral infarction. Consequently, known methods used for early diagnosis of the status of the inner walls of blood vessels include diagnostic methods using echo ultrasound from outside the body, and diagnostic methods comprising inserting a catheter having a measuring probe attached thereto into a blood vessel.

There are several types of the above-mentioned plaque, including those having a lipid core composed of cholesterol and atheromas formed from leukocytes and their remains. In the case an atheroma, which is one type of plaque, is ruptured due to some form of pressure or separates from a blood vessel wall, serious disorders such as cerebral infarction are known to be induced at a high probability. Therefore, it is desirable to identify the type of plaque in order to more accurately diagnose the status of blood vessel wall blood vessel walls, and in response to this desire, plaque identification methods have been examined in the manner of those described in Patent Documents 1 and 2, for example. For example, Patent Document 1 discloses a method of inferring the compositions of plaque from the hardness of the plaque determined on the basis of changes in shape caused by pulsation by continuously observing the plaque with a measuring probe inserted into a blood vessel. In addition, Patent Document 2 discloses a method of inferring the composition of plaque by illuminating light components having two or more different types of properties onto a measured portion, receiving the reflected/scattered light from the measured portion, creating a phantom of each optical plaque, and comparing measurement results for the plaque obtained by echo ultrasound with this phantom.

CITATION LIST

Patent Document

Patent Document 1: Japanese Patent Application Laid-Open No. 2004-329550
Patent Document 2: Japanese Patent Application Laid-Open No. 2007-185242
Patent Document 3: WO 2009/028013 A1

Non-Patent Document

Non-Patent Document 1: Chenan Xia, et al., "Mid-infrared supercontinuum generation to 4.5 μm in ZBLAN fluoride fibers by nanosecond diode pumping", Optics Letters, Vol. 31, No. 17, pp. 2553-2555, Sep. 1, 2006.

DISCLOSURE OF THE INVENTION

Problems that the Invention is to Solve

The present inventors have examined conventional plaque identification methods as described above, and as a result, have discovered the following problems.

Namely, in the identification method described in the above-mentioned Patent Document 1, the patient is subjected to a considerable burden to the invasive nature of the examination resulting from inserting a measuring apparatus into a blood vessel. In addition, since the potential for damage to the inner walls of blood vessels and plaque by the measuring apparatus per se inserted into a blood vessel cannot be ruled out, there is considerable risk accompanying the examination. In addition, in the identification method described in the above-mentioned Patent Document 2, there is no disclosure regarding the specific method by which the plaque phantom is formed, and it is therefore considered to be difficult to create a phantom corresponding to the type of plaque. Consequently, accurate identification of the type of substance attached to a blood vessel wall such as plaque is considered to be difficult with the identification method described in Patent Document 2.

The present invention has been developed to eliminate the problems described above. It is an object of the present invention to provide a blood vessel wall analyzing apparatus provided with a structure for accurately measuring plaque component of the inner walls of blood vessels in a state that reduces the burden on the patient, and a blood vessel wall analyzing method.

Means for Solving the Problems

In order to achieve the above-mentioned object, the blood vessel wall analyzing apparatus according to the present invention is used to analyze compositions of a measured portion within a blood vessel, and more specifically, is provided with illuminating means, detecting means and analyzing means.

The illuminating means illuminates at least a light component in a measurement wavelength range from 780 nm to 2750 nm onto a measured portion within a blood vessel. In addition, the illuminating means includes a light illuminating unit installed at a location a predetermined distance away from the blood vessel, and a light source that supplies the light component to be illuminated onto the measured portion through the light illuminating unit. The detecting means includes a light entering unit installed at a location, at a predetermined distance away from the blood vessel, where a light component from the measured portion reaches, and a light receiving unit that detects the light component introduced through the light entering unit. The analyzing means analyzes compositions of the measured portion based on intensity information on the light component detected by the detecting means.

In particular, in the blood vessel wall analyzing apparatus according to the present invention, one of the illuminating means and the detecting means contains a spectroscope. Namely, as one aspect of the blood vessel wall analyzing apparatus, in the case the illuminating means contains a spectroscope arranged in the light path between the light source and the light illuminating unit, the spectroscope separates, from light directed from the light source toward the light illuminating unit, the light component within the detection wavelength range that is included in the measurement wavelength range and is narrower than the measurement wavelength range. In addition, in the detecting means in this aspect, the light entering unit coincides with a light receiving surface of the light receiving unit. On the other hand, as another aspect of the blood vessel wall analyzing apparatus, in the case the detecting means contains a spectroscope arranged in the light path between the light entering unit and the light receiving unit, the spectroscope separates the light component within the detection wavelength range that is included in the measurement wavelength range and is narrower than the measurement wavelength range, from lights (reflected components or transmitted components) introduced from the measured portion through the light entering unit.

In accordance with the blood vessel wall analyzing apparatus having a structure as described above, although measurement light is illuminated onto a measured portion within a blood vessel by the illuminating means provided outside the blood vessel, a light component from the measured portion is detected by the detecting means provided outside the blood vessel. Thus, the status of a blood vessel wall can be analyzed without inserting an apparatus involved in measurement into the blood vessel. Namely, analyses can be carried out in a state that reduces the burden on a patient. In addition, analyses for distinguishing the compositions of plaque and the like can be carried out using an analyzing apparatus provided outside a blood vessel by measurement that uses the light component (measurement light) contained in the measurement wavelength range from 780 nm to 2750 nm that demonstrates different properties according to compositions of substances such as plaque adhered within the blood vessel.

Here, as an example of a specific configuration that effectively demonstrates the action described above, in the case of the blood vessel wall analyzing apparatus having a structure in which a spectroscope is contained in the illuminating means, one of the light emitting unit in the illuminating means and the light receiving unit in the detecting means is preferably arranged on the epidermis of the neck, while the other is preferably arranged in the esophagus. In addition, as another example of a specific configuration that effectively demonstrates the action described above, both the light emitting unit in the illuminating means and the light receiving unit in the detecting means may be arranged on the epidermis of the neck. Moreover, as still another example of a specific configuration that effectively demonstrates the action described above, both the light emitting unit in the illuminating means and the light receiving unit in the detecting means may be arranged in the esophagus.

On the other hand, in the case of the blood vessel wall analyzing apparatus having a structure in which the spectroscope is included in the detecting means, the spectroscope is arranged in the light path between the light entering unit for introducing the light component from the measured portion and the light receiving portion. In this aspect as well, one of the light illuminating portion and the light entering portion is arranged in the esophagus while the other is arranged on the epidermis of the neck. In addition, both the light illuminating portion and the light entering portion may be arranged on the epidermis of the neck or both may be arranged in the esophagus.

In the blood vessel wall analyzing apparatus according to the present invention, the analyzing means may calculate a second derivative according to wavelength of intensity information (such as the intensity spectrum within each detection wavelength range) on a light component from a measured portion detected by the detecting means within the wavelength range from 1400 nm to 1850 nm or from 1900 nm to 2700 nm, and may analyze compositions of the measured portion based on a result thereof.

The inventors of the present invention found that, in the case of illuminating the light component within the wavelength range from 1400 nm to 1850 nm or from 1900 nm to 2700 nm, a light component that passes through or is reflected by plaque and the like adhered to a blood vessel wall demonstrates a characteristic intensity according to the compositions thereof. Thus, by calculating a second derivative according to wavelength of intensity information on the light component from the measured portion within the detection wavelength range from 1400 nm to 1850 nm or from 1900 nm to 2700 nm, compositions of a substance adhered to the blood vessel wall at the measured portion can be analyzed more accurately.

Furthermore, in the blood vessel wall analyzing apparatus according to the present invention, the detecting means may detect the light component in the detection wavelength range which extends 15 nm on both short and long sides of the selected center wavelength, with each of one or more center wavelengths being selected from the wavelength group comprised of 1514, 1574, 1626, 1691, 1740, 1972, 2055, 2166, 2290, 2465 and 2544 nm. In this case, the analyzing means can analyze for the presence or absence of thrombi in the blood vessel for the analysis of compositions of the measured portion. In addition, the detecting means may also detect the light component in the detection wavelength range which extends 15 nm on both short and long sides of the selected center wavelength, with each of one or more center wavelengths being selected from the wavelength group comprised of 1696, 1717, 2272 and 2629 nm. In this case, the analyzing means can analyze for the presence or absence of an atheroma in a blood vessel for the analysis of compositions of the measured portion. Moreover, the detecting means may also detect the light component in the detection wavelength range which extends 15 nm on both short and long sides of the selected center wavelength, with each of one or more center wavelengths being selected from the wavelength group comprised of 1690, 2294 and 2372 nm. As a result, the analyzing means can analyze for the presence or absence of a lipid core in a blood vessel for the analysis of compositions of the measured portion.

In addition, the blood vessel wall analyzing apparatus according to the present invention may further comprises display means that displays an analysis result by the analyzing means.

The blood vessel wall analyzing method according to the present invention is a method of analyzing compositions of the measured portion in the blood vessel by using the blood vessel wall analyzing apparatus having the previously described configuration, and is used in a state in which the light emitting end is inserted so as to be positioned near the measured portion, and the light entering end is installed at a predetermined position in the blood vessel where the light component from the measured portion reaches.

In a specific measurement process, the light component at least in the measurement wavelength range of 780 nm to 2713 nm is illuminated onto the measured portion through the light emitting end, and the light component that has entered through the light entering end is detected from the measured portion. Analysis data is generated for identifying the composition of the measured portion from intensity information on the detected light component. The generated data is used in various processing such as analysis of compositions of the measured portion or displaying on a monitor.

Specific analysis data is obtained by calculating a second derivative according to wavelength of intensity information on a light component from the measured portion detected by the detecting means of the blood vessel wall analyzing apparatus having a structure like that previously described within the detection wavelength range of, for example, 1400 nm to 1850 nm or 1900 nm to 2700 nm. The analyzing means analyzes compositions of the measured portion based on a result thereof.

In addition, the blood vessel wall analyzing method according to the present invention overlays image information relating to the composition of the measured portion onto a two-dimensional tomographic image of the blood vessel, and display the resulting two-dimensional image on a monitor.

Effects of the Invention

In accordance with the blood vessel wall analyzing apparatus and blood vessel wall analyzing method according to the present invention, plaque components of an inner wall of a blood vessel can be accurately measured in a state that reduces the burden on a patient.

BRIEF DESCRIPTION OF THE DRAWINGS

FIG. 3 is a drawing for explaining various positional relationships of a light emitting unit in illuminating means and a light receiving unit in detecting means;

FIG. 12 shows the absorption spectra (second derivative) of thrombus and blood.

BEST MODES FOR CARRYING OUT THE INVENTION

Figure 1:
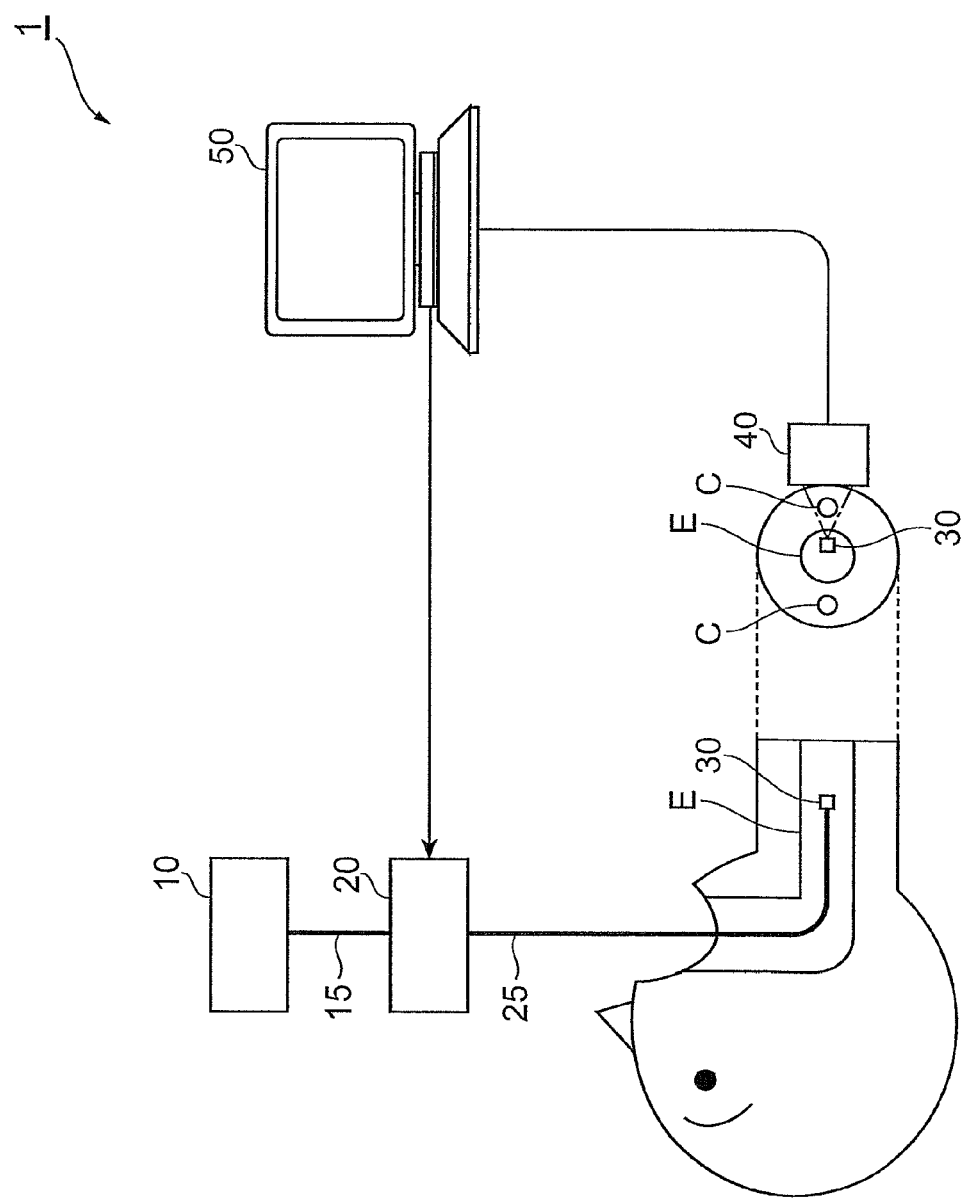
FIG. 1 is a drawing showing the configuration of an embodiment of a blood vessel wall analyzing apparatus according to the present invention.

In the following, embodiments of the blood vessel wall analyzing apparatus and blood vessel wall analyzing method according to the present invention will be explained in detail with reference to FIGS. 1 to 13. In the description of the drawings, identical or corresponding components are designated by the same reference numerals, and overlapping description is omitted.

Configuration of Blood Vessel Wall Analyzing Apparatus

FIG. 1 is a drawing showing the configuration of an embodiment of the blood vessel wall analyzing apparatus according to the present invention. As shown in FIG. 1, a blood vessel wall analyzing apparatus 1 is an analyzing apparatus that can be applied to one embodiment of the blood vessel wall analyzing method according to the present invention, and is provided with a light source 10, a spectroscope 20, a light illuminating unit 30, a light receiving unit 40, and an analysis unit 50. In addition, the light source 10 and the spectroscope 20, and the spectroscope 20 and the light illuminating unit 30, are connected by the optical fibers 15 and 25, respectively. The light receiving unit 40 and the analysis unit 50 are electrically connected, and the analysis unit 50 and the spectroscope 20 are also electrically connected. In the blood vessel wall analyzing apparatus 1 according to the present embodiment, the light source 10, the spectroscope 20 and the light illuminating unit 30 compose illuminating means that illuminates measurement light onto a measured portion from outside a blood vessel. The light receiving unit 40 and the analysis unit 50 compose detecting means that detects a light component from the measured portion. The analysis unit 50 functions as analyzing means for analyzing compositions of the measured portion based light detected by the detecting means, and as display means for displaying analysis results obtained from the analyzing means.

The light source 10 is a light source that outputs a light component that contains the measurement wavelength range of near infrared light from 780 nm to 2750 nm, and for example, a laser diode (LD) light source or a supercontinuum (SC) light source as described in the above-mentioned Non-Patent Document 1 is used preferably. The light component outputted from the light source 10 is guided to the spectroscope 20 through the optical fiber 15.

The spectroscope 20 is inputted with the light component from the light source 10 that has propagated through the optical fiber 15, and outputs to the optical fiber 25 only a light component within a detection wavelength range centering on a specific wavelength based on instructions from the analysis unit 50. A diffraction grating or variable wavelength filter and the like is used for the spectroscope 20. In addition, in the case of using a diffraction grating for light entering from the light source 10 based on instructions from the analysis unit 50, the spectroscope 20 outputs a light component of a specific wavelength within a working detection wavelength range to the optical fiber 25 by altering the inclination of the diffraction grating. The light component outputted from the spectroscope 20 is guided to the light illuminating unit 30 through the optical fiber 25.

The light illuminating unit 30 is inserted into an esophagus E when analyzing a blood vessel wall with the blood vessel wall analyzing apparatus 1. A light component from the spectroscope 20 that has propagated through the optical fiber 25 is illuminated as measurement light onto a measured portion within a carotid artery C from within the esophagus E.

The light receiving unit 40 receives light outputted from the light illuminating unit 30 that has been illuminated onto a measured portion within the carotid artery C and has passed through the measured portion. The light receiving unit 40 can use a light receiving element such as a photodiode that converts light from the measured portion into an electric current and transmits that electric current to the analysis unit 50.

Furthermore, light may also be converted to electric current by providing a light entering end surface of an optical fiber for the light receiving unit 40, propagating the light that has entered the light entering end surface of the optical fiber, and using light receiving element provided at a different position than the light receiving unit 40.

The analysis unit 50 analyzes a composition of a measured portion based on intensity data of a light component received by the light receiving unit 40, and displays the result on a monitor and the like. More specifically, the analysis unit 50 is comprised of a personal computer (PC) or workstation (WS) and the like, and is at least provided with display means such as a monitor, arithmetic processing means, input/output means and recording means. As a specific example of analysis carried out by the analysis unit 50, the analysis unit 50 calculates the intensity of light received by the light receiving unit 40 for each wavelength based on the magnitude of electric current from a light receiving element of the light receiving unit 40. The analysis unit 50 then determines the intensity spectrum of a light component in a detection wavelength range from the calculation result for each wavelength, carries out second derivation on the intensity spectrum for that wavelength, and analyzes a composition of the measured portion such as plaque based on the size of the peak originating in the composition of the measured portion such as plaque. The analysis result (analysis data) is then notified to a user such as a subject by the PC or WS displaying the result on a monitor and the like. In addition, a PC or WS having the function of the analysis unit 50 may also be provided with a function for controlling the entire blood vessel wall analyzing apparatus 1. Namely, the PC or WS has a function for selecting a wavelength of a light component to be split by the spectroscope 20 (central wavelength of the detection wavelength range) and issuing an instruction to the spectroscope 20.

Figure 2:
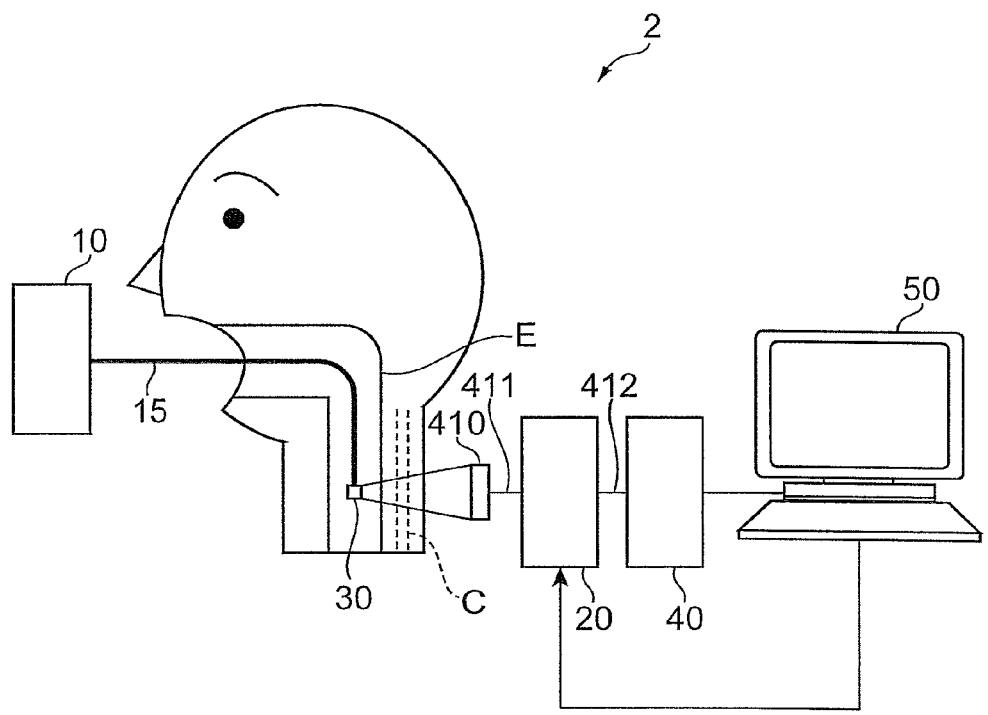
FIG. 2 is a drawing showing the configuration of another embodiment of a blood vessel wall analyzing apparatus according to the present invention.

FIG. 2 is a drawing showing another embodiment of the blood vessel wall analyzing apparatus according to the present invention. As shown in FIG. 2, a blood vessel wall analyzing apparatus 2 is provided with the light source 10, the spectroscope 20, the light illuminating unit 30, the light receiving unit 40 and the analysis unit 50 in the same manner as the blood vessel wall analyzing apparatus 1 of FIG. 1. However, the blood vessel wall analyzing apparatus 2 of the present embodiment differs from the blood vessel wall analyzing apparatus 1 of FIG. 1 in which the spectroscope 20 is arranged on the side of the illuminating means in that the spectroscope 20 is arranged on the side of the detecting means. The blood vessel wall analyzing apparatus 2 according to the present embodiment substantially has the same structure as the blood vessel wall analyzing apparatus 1 of FIG. 1 with respect to other compositions.

Namely, in the blood vessel wall analyzing apparatus 2 according to the present embodiment, the detecting means is constituted by a light entering unit 410, the spectroscope 20 and the light receiving unit 40. The illuminating means of the present embodiment has the same structure as the illuminating means in the blood vessel wall analyzing apparatus 1 of FIG. 1 with the exception that it does not contain the spectroscope 20.

In the blood vessel inner vessel analyzing apparatus 2, a light component from the light emitting unit 30 that has passed through a measured portion reaches the light entering unit 410. The light entering unit 410 is optically connected to the spectroscope 20 through an optical fiber 411, and the light component that has entered through the light entering unit 410 propagates through the optical fiber 411 and reaches the spectroscope 20. In the spectroscope 20, only a light component within the detection wavelength range centering on a specific wavelength is output in accordance with an instruction from the analyzer 50. The spectroscope 20 and the light receiving unit 40 are optically connected through an optical fiber 412, and output light from the spectroscope 20 propagates through the optical fiber 412 and reaches the light receiving unit 40. The operation of the light receiving unit 40 and the analysis unit 50 are the same as that of the previously described blood vessel wall analyzing apparatus 1 of FIG. 1.

Furthermore, the positional relationship between the light emitting unit 30 in the illuminating means and the light receiving unit 40 in the detecting means in the blood vessel wall analyzing apparatus 1 of FIG. 1 is not limited to the relationship shown in FIG. 1, but rather may employ the opposite arrangement. In addition, as indicated in the area (A) of FIG. 3, both the light detecting unit 30 and the light receiving unit 40 may be arranged on the epidermis of the neck. As shown in the area (B) of FIG. 3, both the light detecting unit 30 and the light receiving unit 40 may also be arranged in the esophagus. However, in the case of the blood vessel wall analyzing apparatus 2 of FIG. 2, the light entering unit 410 instead of the light receiving unit 40 is arranged in the manner described above with respect to the relationship with the light illuminating unit 30.

Figure 4:
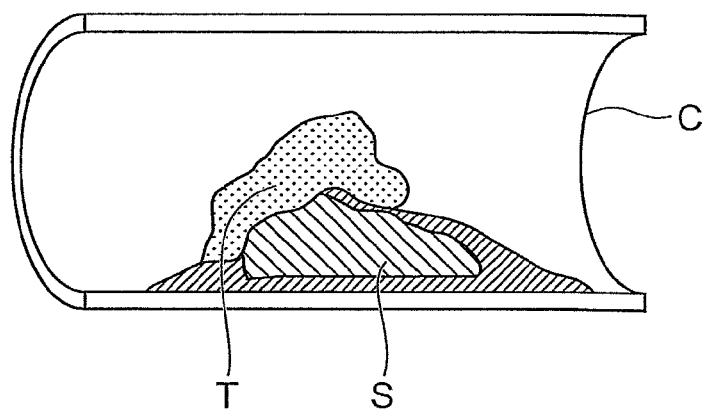
FIG. 4 is a drawing for explaining plaque on the inner wall of a blood vessel.

Measurement targets of the blood vessel wall analyzing apparatus 1 shown in FIG. 1 include plaque, thrombi and hematomas adhered to the inner wall of the carotid artery C. Four typical examples of plaque adhered to the inner wall of the carotid artery C include lipid cores comprised of cholesterol, atheromas formed from leukocytes and their remains, calculi resulting from the calcification of cholesterol-like substances, and fibrous layers covering the surface of plaque comprised of the three components listed above and having collagen as the main component thereof. In addition, thrombi and hematomas comprised of blood clots within blood vessels also have the potential to be involved in brain diseases. FIG. 4 is a drawing schematically showing an example of the case of plaque S and a thrombus T adhered to the inner wall of the carotid artery C. In the case the plaque S and thrombus T have adhered to the inner wall of the carotid artery C, since the blood vessel diameter in the area of the carotid artery C where blood is able to flow through becomes narrow as shown in FIG. 4, this is known to cause stenosis and obstruction of the carotid artery C as well as cerebral infarction or cerebral ischemia and the like. Among the typical types of plaque described above, atheromas in particular are known to have the highest potential to cause cerebral infarction, while on the other hand, since calculi and lipid cores have a low frequency of separating from the inner wall of the carotid artery C, plaque comprised of these components is known to have a low risk of obstructing intracerebral blood vessels and the like. Consequently, in order to more accurately determine the risk of occurrence of diseases such as cerebral infarction, it is thought to be necessary to identify the compositions of plaque adhered to the inner wall of the carotid artery C.

Whether or not plaque is adhered to the inner wall of the carotid artery C can be determined by measuring using diagnostic methods such as echo ultrasound diagnosis or intravascular ultrasound (IVUS) from outside the neck. However, in the case of echo ultrasound diagnosis or intravascular ultrasound, it is difficult to obtain information other than that relating to the shape of the plaque within the blood vessel, namely to identify plaque compositions. In addition, although thrombi and hematomas adhered to the inner wall of the carotid artery C and comprised of blood clots within blood vessels are also measurement targets of the blood vessel wall analyzing apparatus 1 since they also have the potential to be involved in brain diseases, their detection is difficult from outside the neck when using echo ultrasound or intravascular ultrasound.

In contrast, use of the blood vessel wall analyzing apparatus 1 according to the present embodiment makes it possible to detect plaque, thrombi and hematomas formed in the carotid artery C and identify their components, and the following provides an explanation of this using the measurement examples indicated below.

Examples of Measurement Using Blood Vessel Wall Analyzing Apparatus

Measurement Example 1

Figure 5:
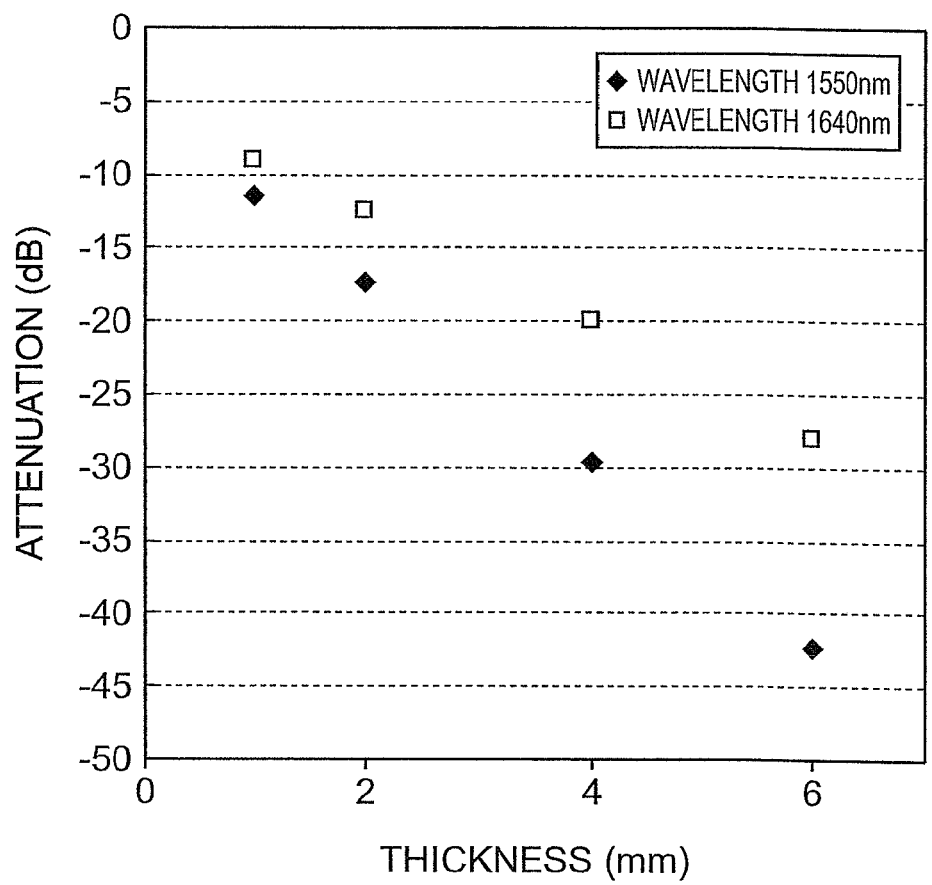
FIG. 5 is a drawing showing the results of evaluating attenuation of light that has passed through pork using a simulation.

The results of calculating attenuation of transmitted light in the case of illuminating near infrared light onto pork used as a measurement target by Monte Carlo simulation are shown in FIG. 5. More specifically, infrared light at wavelengths of 1550 nm and 1640 nm was illuminated onto pork having a thickness of 6 mm under conditions of a temperature of 38° C. followed by measurement of absorption coefficient and scattering coefficient. Attenuation of the transmitted light when the near infrared light was illuminating onto the pork was calculated from the results by Monte Carlo simulation. Furthermore, the reason for making the thickness of the measurement target to be 6 mm was that the thickness equivalent to the epidermis on the outside of the human esophagus and carotid artery and muscle layers containing blood vessel walls present in the light path is about 6 mm. As a result of the simulation, the attenuation of the transmitted light was −42 dB in the case of light at the wavelength of 1550 nm and −28 dB in the case of light at the wavelength of 1640 nm.

Measurement Example 2

Figure 6:
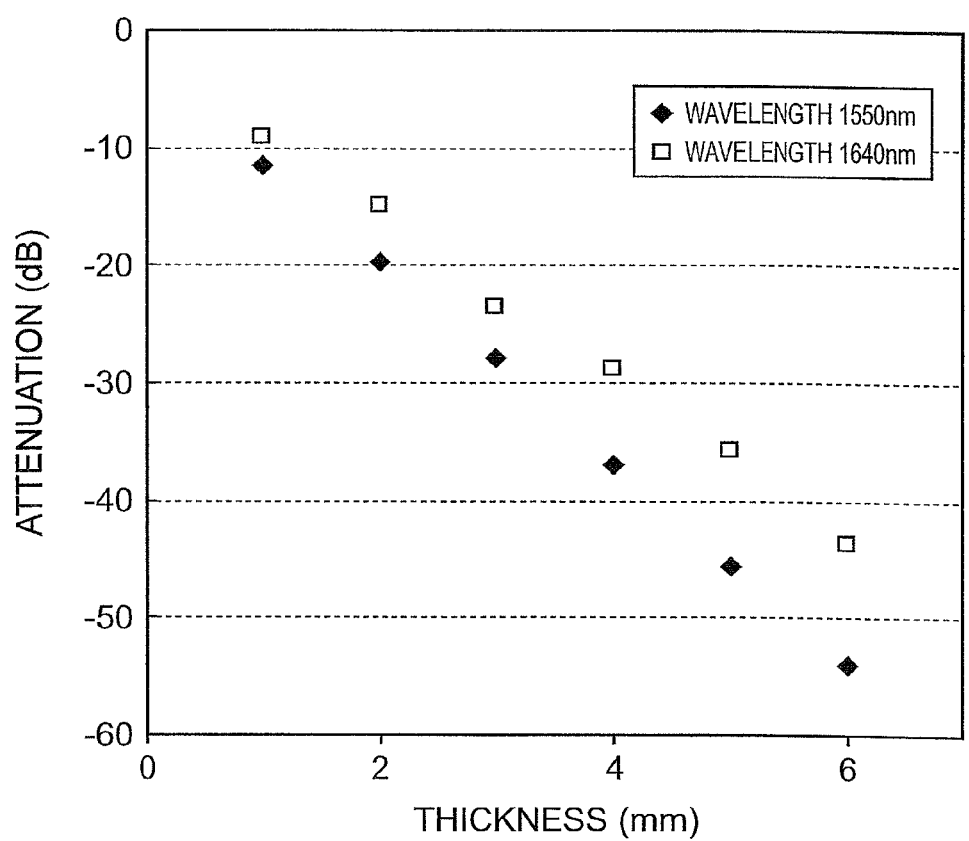
FIG. 6 is a drawing showing the results of measuring attenuation of light that has passed through pork.

Attenuation of transmitted light was measured in the case of illuminating near infrared light onto actual pork for the purpose of confirming the simulation results of Measurement Example 1. The results are shown in FIG. 6. Measurement conditions were similar to those of Measurement Example 1, and although near infrared light (parallel light) having a diameter of 1 mm was illuminated onto pork having a thickness of 6 mm under conditions of a temperature of 38° C., the transmitted light was received by arranging a multimode fiber having a core diameter of 400 μm on the opposite side of the pork from the side illuminated with near infrared light. Attenuation was then determined from the intensity thereof. Two types of light having the wavelengths of 1550 nm and 1640 nm were illuminated as near infrared light. As a result, the light was confirmed to be attenuated in the same manner as the simulation results determined in Measurement Example 1.

Measurement Example 3

The intensity of light that passed through muscle was measured using a pork muscle layer in the above-mentioned Measurement Examples 1 and 2. In Measurement Examples 3 and 4, the intensity of light that passed through fat was measured using a pork fat layer.

Figure 7:
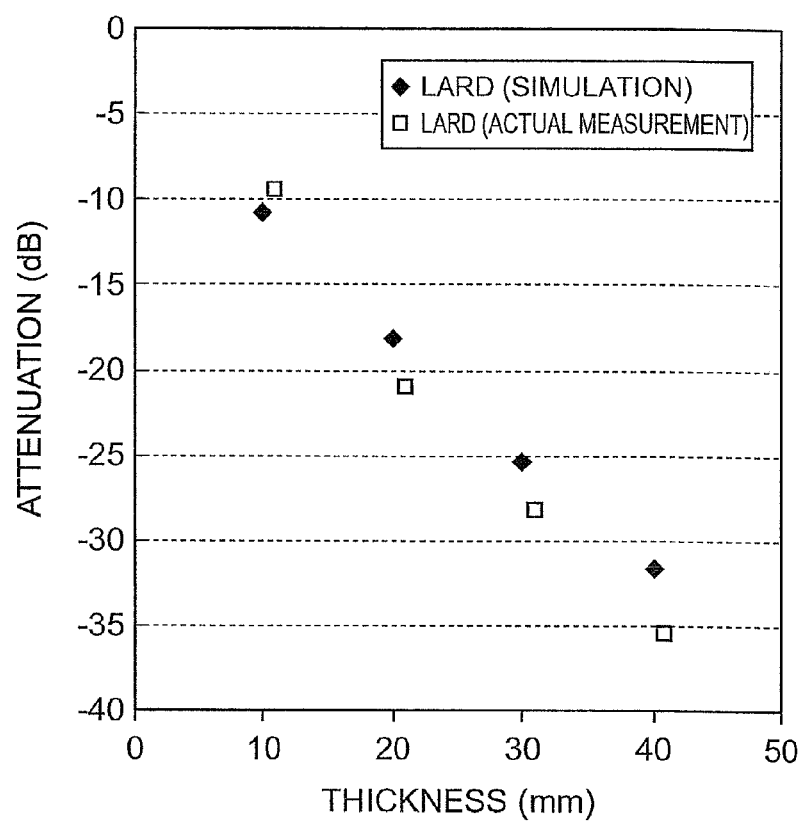
FIG. 7 is a drawing showing the results of evaluating and measuring attenuation of light that has passed through lard using a simulation.

The results of calculating the attenuation of transmitted light in the case of illuminating near infrared light onto pork fat (lard) used for the measurement target by Monte Carlo simulation are shown in FIG. 7. More specifically, near infrared light of the wavelength of 1550 nm was illuminated onto lard having a thickness of 40 mm under conditions of a temperature of 38° C. followed by measurement of absorption coefficient and scattering coefficient. Attenuation of the transmitted light when the lard was illuminated with the infrared light was then calculated from the results by Monte Carlo simulation. Furthermore, the reason for making the thickness of the lard used for the measurement target to be 40 mm is that the thickness equivalent to the epidermis on the outside of the human esophagus and carotid artery and a fat layer present in the light path is about 40 mm. As a result of the simulation, attenuation of the transmitted light was −32 dB.

Measurement Example 4

Attenuation of transmitted light was measured in the case of illuminating near infrared light onto actual lard for the purpose of confirming the simulation results of Measurement Example 3. The results are shown in FIG. 7. Measurement conditions were similar to those in Measurement Example 3, near infrared light (parallel light, wavelength: 1550 nm) having a diameter of 1 mm was illuminated onto lard having a thickness of 40 mm under conditions of a temperature of 38° C., and the transmitted light was received by arranging a multimode fiber having a core diameter of 400 μm on the opposite side of the lard from the side illuminated with near infrared light. Attenuation was then determined from the intensity thereof. As a result, the light was confirmed to be attenuated in the same manner as the simulation results determined in Measurement Example 3.

Signals can be output to −100 dBm in measurements using existing near infrared detecting elements. Here, the light component of 1 mW (0 dBm), which is an intensity that does not have a detrimental effect on the human body, is emitted from a light source within the esophagus and detected by a near infrared detecting element arranged on the epidermis of the neck. In this case, light of intensity sufficiently higher than −100 dBm is thought to be detected at the epidermis of the neck based on the results of Measurement Examples 1 to 4.

However, in the case of using an SC light source for the light source 10, the output after beam splitting is typically about −10 dB to −20 dB. In addition, attenuation attributable to the spectroscope is typically −15 dBm to −25 dBm. Since the amount of light that has passed through fat and muscle of the human neck is −73 dB at the wavelength of 1550 nm based on the simulation results, when the SC light source or splitter is used as a light source the amount of transmitted light becomes −83 dBm to −93 dBm, which ends up approaching the detection limit of near infrared detecting elements. On the other hand, the amount of transmitted light in the case of the wavelength of 1640 nm is expected to increase by 14 dBm or more as compared with that at a wavelength of 1550 nm based on the simulation results of light passing through muscle, thereby making it possible to obtain an output that is higher by at least one digit than the detection limit of near infrared detecting elements. Thus, in a configuration in which the light emitting unit or the light receiving unit is arranged on the epidermis of the neck while the other is arranged in the esophagus, in the case of using a SC light source for the light source, a detecting apparatus that uses a light component having the wavelength of 1600 nm or more is more desirable.

Measurement Example 5

A simulation model was constructed that simulated the structure of the neck from the epidermis of neck to the inner wall of the esophagus E by assuming the case of the light illuminating unit 30 of the blood vessel wall analyzing apparatus 1 being arranged within the esophagus E and the light receiving unit 40 being arranged on the epidermis of the neck.

Figure 8:
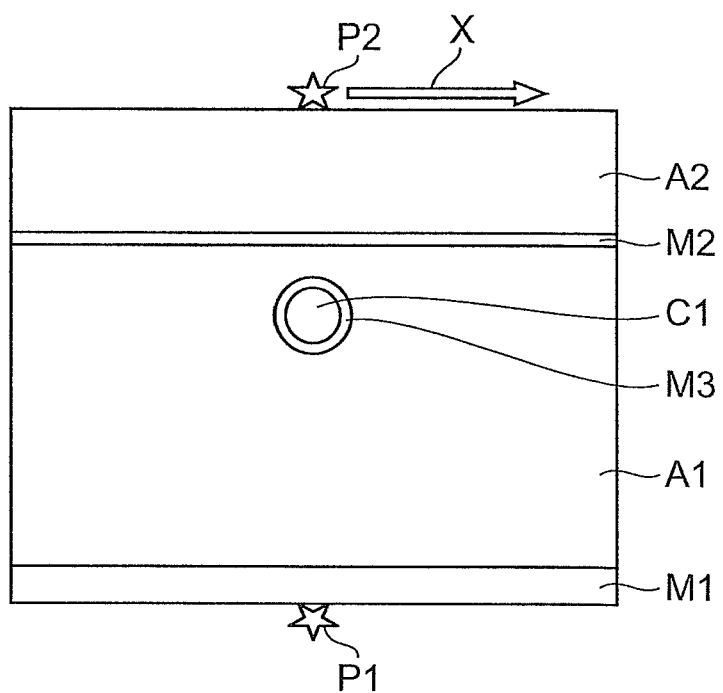
FIG. 8 is a drawing for explaining a simulation model used to measure light intensity when near infrared light was illuminated onto a carotid artery.

The intensity of light output to the epidermis of the neck by passing through the carotid artery C was simulated in the case measurement light had entered from the esophagus inner wall. The specific simulation model is shown in FIG. 8. As shown in FIG. 8, a light source P1 is arranged in the esophagus inner wall (bottom of the drawing), and a light receiving unit P2 is arranged on the epidermis of the neck (top of the drawing). An esophagus wall M1 comprised of muscle having a thickness of 3 mm, a fat layer A1 having a thickness of 26 mm, a muscle layer M2 having a thickness of 1 mm, and a fat layer A2 having a thickness of 10 mm were laminated in order from the esophagus inner wall towards the epidermis of the neck, and the light source P1 and the light receiving unit P2 were arranged in the direction perpendicular to the esophagus inner wall and neck epidermis so as to interpose a blood layer C1 simulating a carotid artery provided within the fat layer A1 in opposition thereto such that the distance between the esophagus inner wall and the neck epidermis was 40 mm. The blood layer C1 was in the shape of a circle having a diameter of 5 mm, and the periphery thereof was covered by a vessel wall M3 comprised of muscle having a thickness of 1 mm. At this time, the distance between the boundary of the esophagus wall M1 and the fat layer A1 and the boundary of the vessel wall M3 and the fat layer A1 on the side of the light source P1 was 15 mm, and the distance between the boundary of the vascular wall M3 and the fat layer A1 on the side of the light receiving unit P2 and the light receiving unit P2 was 15 mm. In addition, the diameter of the light receiving unit P2 was 2 mm.

As a result of using the absorption coefficient and scattering coefficient to simulate the intensity of light having the wavelength of 1600 nm received by the light receiving unit P2 after having been outputted from the light source P1 and passed through the blood layer C1 using the above-mentioned simulation model, attenuation of the received light was −73 dB. Thus, in the case of having received near infrared light at the epidermis after illuminating towards the carotid artery C from within the esophagus E using the blood vessel wall analyzing apparatus 1 according to the present embodiment, results indicating that the transmitted light can be measured at an intensity sufficient for measurement were obtained by simulation.

Figure 9:
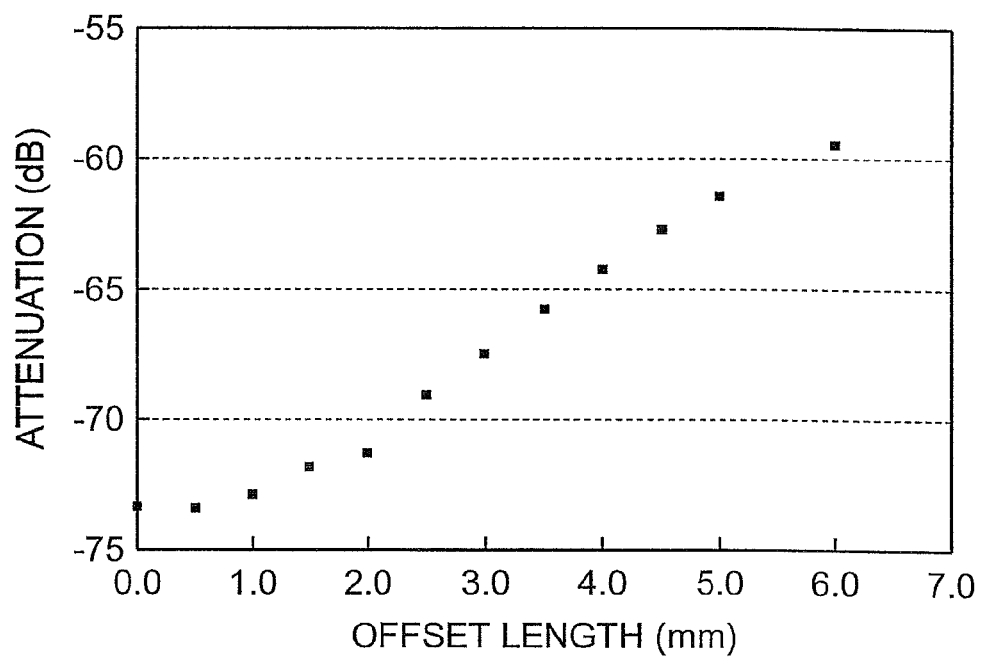
FIG. 9 is a drawing showing the results of evaluating attenuation of light in the case of having moved the position of a light receiving unit in a simulation.

Next, the results of having determined the relationship between an offset length and light attenuation are shown in FIG. 9 in the case of offsetting the light receiving unit P2 in the X direction shown in FIG. 8 for the purpose of more aggressively obtaining light transmitted through the vessel wall from the location of the light receiving unit P2 of FIG. 8. In this manner, attenuation of light received by the light receiving unit P2 was confirmed to decrease more.

Measurement Example 6

Figure 10:
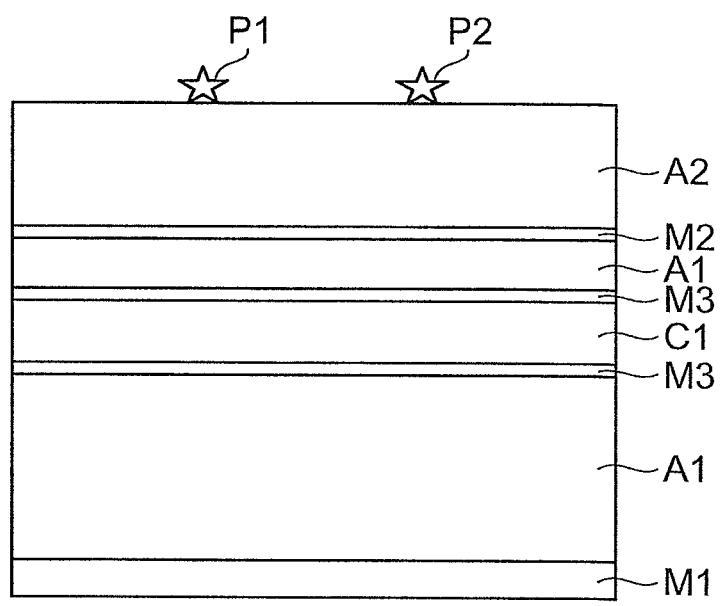
FIG. 10 is a drawing for explaining a simulation model used to measure light intensity when near infrared light was illuminated onto a carotid artery.

Light intensity was calculated by simulation in a configuration in which light that has entered from the epidermis returns again to the epidermis after repeatedly undergoing multiple scattering using a simulation model similar to the simulation model shown in Measurement Example 5. Although the simulation model shown in FIG. 10 is the same as the simulation model shown in FIG. 8, in contrast to a state in which the blood layer C1 is extending in a direction perpendicular to the paper in FIG. 8, in FIG. 10, the case is shown in which the blood layer C1 extends within the plane of the paper. The simulation model shown in FIG. 10 differs from that of Measurement Example 5 in that both the light source P1 and the light receiving unit P2 are arranged on the side the epidermis of the neck (top of the drawing), and both are located at positions 30 mm apart along the blood layer C1. As a result of using the absorption coefficient and scattering coefficient to simulate light received by the light receiving unit P2 having a diameter of 2 mm in the case of illuminating light of the wavelength of 780 nm from the light source P1 towards the blood layer C1 using this simulation model, attenuation of the received light was 87 dB. Thus, in the case of having received near infrared light at the epidermis after illuminating towards the carotid artery C from the neck epidermis using the blood vessel wall analyzing apparatus 1 according to the present embodiment, results indicating that the transmitted light can be measured at an intensity sufficient for measurement were obtained by simulation.

Measurement Example 7

Figure 11:
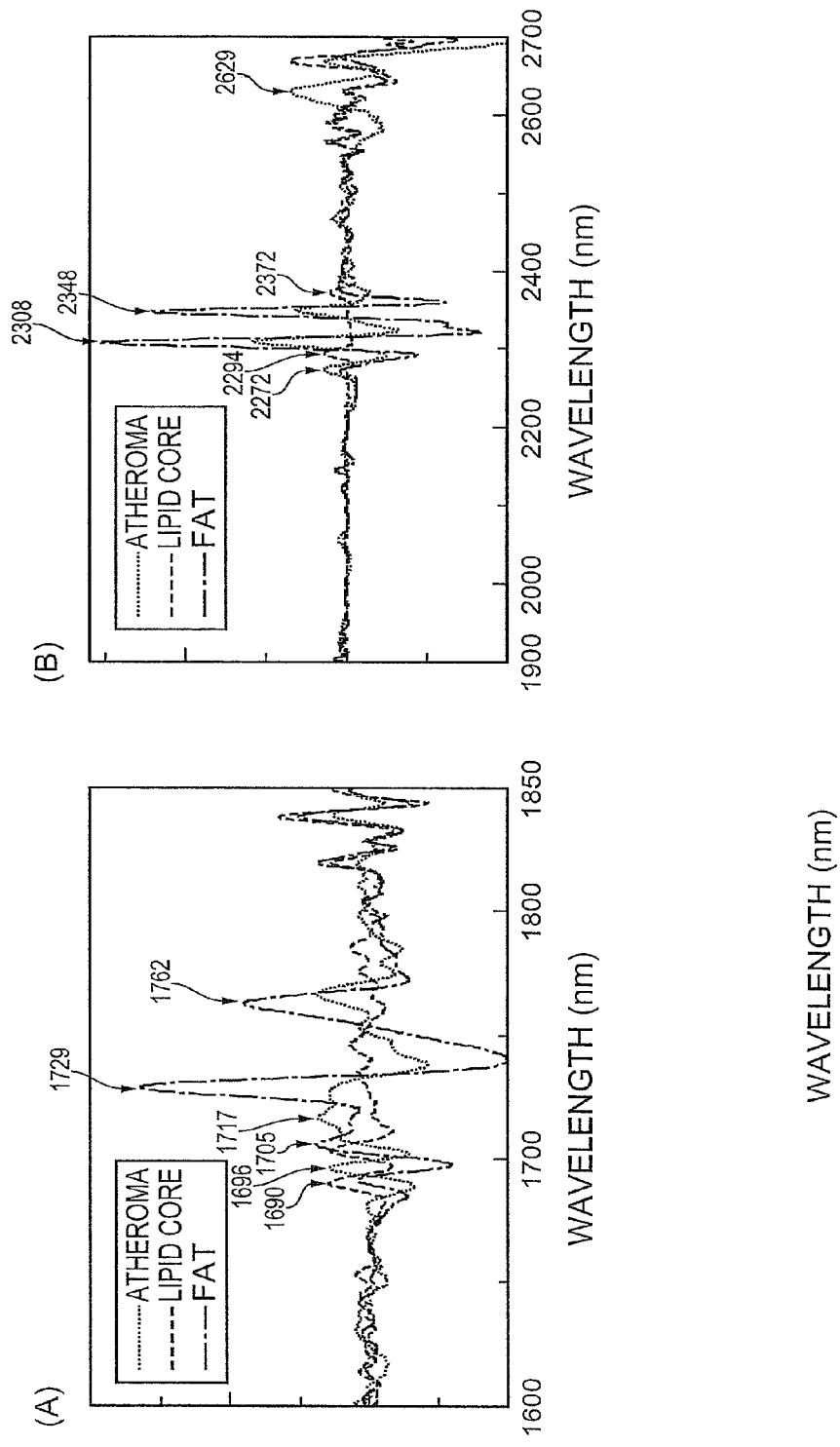
FIG. 11 shows the absorption spectra (second derivative) of plaque (lipid core, atheroma) and fat.

The results of measuring absorption spectra in the case of respectively illuminating near infrared light onto plaque compositions consisting of an atheroma and lipid core and comparing with the absorption spectrum of fat are shown in FIG. 11. More specifically, near infrared light within the measurement wavelength range from 1600 nm to 2700 nm was respectively illuminated onto an atheroma, lipid core and fat followed by measurement of the absorption spectra thereof, determining the second derivative according to wavelength of the absorption spectra within each measurement wavelength range from 1600 nm to 1850 nm and from 1900 nm to 2700 nm, and comparing the results. Furthermore, in FIG. 11, the area (A) shows the second derivative according to wavelength of absorption spectra within the measurement wavelength range from 1600 nm to 1850 nm, while the area (B) shows the second derivative according to wavelength of absorption spectra within the measurement wavelength range from 1900 nm to 2700 nm. As shown in FIG. 11, a plurality of characteristic peaks thought to be effective for differentiating the atheroma and lipid core from fat (such as those at 1690, 1696, 1705, 1717, 1729, 1762, 2272, 2294, 2308, 2348, 2372 and 2629 nm) were confirmed to be present in the absorption spectra (second derivative) of the atheroma and lipid core in each of the above-mentioned measurement wavelength ranges.

In particular, the presence or absence of an atheroma in the blood vessel can be analyzed in the case of using the light component within the detection wavelength range which extends 15 nm on both short and long sides of the selected center wavelength, with each of one or more center wavelengths being selected from the wavelength group comprised of peak wavelengths of 1696, 1717, 2272 and 2629 nm for analyzing compositions of a measured portion. In addition, the presence or absence of a lipid core in the blood vessel can be analyzed in the case of using the light component within the detection wavelength range which extends 15 nm on both short and long sides of the selected center wavelength, with each of one or more center wavelengths being selected from the wavelength group comprised of peak wavelengths of 1690, 2294 and 2372 nm for analyzing compositions of a measured portion. In consideration of the relationship between the peak wavelengths of an atheroma and the peak wavelength of a lipid core as indicated above, the use of the peak wavelength of 2629 nm, at which the peak wavelength of a lipid core and the like is not present in the vicinity thereof, is more preferable for analyzing for the presence or absence of an atheroma. On the other hand, the peak wavelength of 2294 nm of a lipid core overlaps with a peak wavelength of fat and the like, while strong peak wavelengths of fat or atheromas are present within the wavelength range extending several nm on both short and long sides of another peak wavelength of 1690 nm. In consideration thereof, the peak wavelength of 2372 nm is preferable for analyzing for the presence or absence of a lipid core.

Measurement Example 8

The results of measuring absorption spectrum in the case of illuminating near infrared light onto thrombi and comparing with the absorption spectrum of blood are shown in FIG. 12. More specifically, near infrared light within the measurement wavelength range from 1400 nm to 2700 nm was respectively illuminated onto thrombi and blood followed by measurement of the absorption spectra thereof, determining the second derivative according to wavelength of the absorption spectra within each measurement wavelength range from 1400 nm to 1800 nm and from 1900 nm to 2700 nm, and comparing the results. Furthermore, in FIG. 12, the area (A) shows the second derivative according to wavelength of absorption spectra within the measurement wavelength range from 1400 nm to 1800 nm, while the area (B) shows the second derivative according to wavelength of absorption spectra within the measurement wavelength range from 1900 nm to 2700 nm. As shown in FIG. 12, a plurality of characteristic peaks thought to be effective for differentiating thrombi from blood (such as those at 1514, 1574, 1626, 1691, 1740, 1972, 2055, 2166, 2290, 2465 and 2544 nm) were confirmed to be present in the absorption spectra (second derivative) of the thrombi in each of the above-mentioned measurement wavelength ranges.

Thus, the presence or absence of thrombi in a blood vessel can be analyzed by using the light component within the detection wavelength range which extends 15 nm on both short and long sides of the selected center wavelength, with each of one or more center wavelengths being selected from the wavelength group comprised of peak wavelengths of 1514, 1574, 1626, 1691, 1740, 1972, 2055, 2166, 2290, 2465 and 2544 nm for analyzing compositions of a measured portion. Furthermore, the use of the peak wavelengths of 1514, 1626, 1972 and 2465 nm, at which the peak wavelength of blood is not present in the vicinity thereof, is more preferable for analyzing for the presence or absence of thrombi, while the peak wavelengths of 1972 nm and 2465 nm are particularly preferable since there is little effects of attenuation caused by scattering thereon.

In the measurement examples described above, it was confirmed that: (1) it is possible to measure near infrared light by transmitting between an esophagus inner wall comprised of fat and blood within a carotid artery and the epidermis of the neck, (2) it is possible to differentiate between fat and plaque as well as identify the type of plaque (particularly lipid cores and atheromas) in the case of illuminating light within the wavelength range of near infrared light and measuring the absorption spectra, and (3) it is possible differentiate between thrombi and blood in the case of illuminating light within the wavelength range of near infrared light and measuring the absorption spectra. Thus, by arranging the light illuminating unit 30 of the blood vessel wall analyzing apparatus 1 according to the present embodiment within the esophagus E, arranging the light receiving unit 40 on the epidermis of the neck, and illuminating near infrared light from the light receiving unit 30 to the light receiving unit 40 while receiving light that has passed through the measured portion of the carotid artery C, it was confirmed that compositions of substances adhered to the inner wall of the carotid artery C can be evaluated.

Furthermore, in the case of reversing the arrangement of the light illuminating unit 30 and the light receiving unit 40, namely in the case of arranging the light illuminating unit 30 on the epidermis of the neck and arranging the light receiving unit 40 within the esophagus E, compositions of substances adhered to the inner wall of the carotid artery C can be evaluated in the same manner as in the above-mentioned measurement examples.

In addition, in the case of arranging the light illuminating unit 30 and the light receiving unit 40 on the side of the neck epidermis as shown in the above-mentioned Measurement Example 6, it was confirmed that the intensity of light outputted from the light illuminating unit 30 in a configuration in which it again returns to the epidermis after repeatedly undergoing multiple scattering can be measured in the light receiving unit 40. On the basis thereof, even in the case of measuring when arranging both the light illuminating unit 30 and the light receiving unit 40 on the side of the neck epidermis or in the esophagus E while separating by a fixed distance, compositions of substances adhered to the inner wall of the carotid artery C can be evaluated (see FIG. 3).

Although the above-mentioned effects have been explained for the blood vessel wall analyzing apparatus 1 of FIG. 1, similar effects are also demonstrated by the blood vessel wall analyzing apparatus 2 of FIG. 2.

Example of Usage of Blood Vessel Wall Analyzing Apparatus

In accordance with the blood vessel wall analyzing apparatuses 1 and 2 according to the present embodiment, compositions of substances adhered to the inner wall of the carotid artery C can be analyzed as was previously described. Furthermore, the status of carotid artery plaque can be more accurately determined by combining analysis results obtained with the blood vessel wall analyzing apparatuses 1 and 2 with measurement results obtained with other measuring apparatuses. For example, although the blood vessel wall analyzing apparatuses 1 and 2 according to the present embodiment enable analysis of compositions of plaque that has adhered to the inner wall of the carotid artery C, it is difficult to accurately measure the shape of the plaque. Thus, by combining with, for example, echo ultrasound from outside the body, the capacity of the plaque to induce disease, for example, can be more accurately evaluated based on measurement results of the form of the plaque obtained by echo ultrasound and analysis results of compositions of the plaque obtained with the blood vessel wall analyzing apparatuses 1 and 2.

Figure 13:
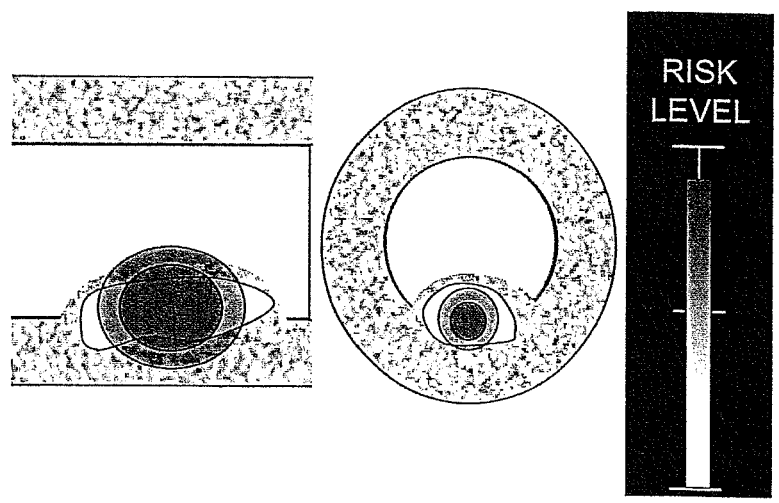
FIG. 13 shows an example of a monitor display of analysis results obtained from a blood vessel wall analyzing apparatus.

In addition, analysis results from the blood vessel wall analyzing apparatuses 1 and 2 are notified to a user such as a subject by displaying on a monitor provided in the analysis unit 50. In the case of displaying analysis results on a monitor and the like in this manner as well, the user can be notified in a more readily understandable manner by displaying these analysis results in combination with measurement results obtained using another measurement method. For example, as shown in FIG. 13, the shape and risk level (capacity to induce disease) can be displayed concurrently based on the shape of the plaque as measured by echo ultrasound from outside the body and on analysis results of plaque compositions obtained with the blood vessel wall analyzing apparatus 1. Furthermore, the blood vessel image capturing apparatus described in the above-mentioned Patent Document 3 is a known example of a apparatus that displays blood vessel tomographic images, including those of plaque measured by ultrasound echo.

As has been previously described, according to the blood vessel wall analyzing apparatuses 1 and 2 according to the present embodiment, together with illuminating measurement light onto a measured portion such as the carotid artery C from the light illuminating unit 30 provided outside a blood vessel, since light from the measured portion is detected in the light receiving unit 40 provided within the blood vessel, the status of the blood vessel wall can be analyzed without inserting a apparatus involved in measurement into the blood vessel. As a result, analyses can be carried out in a state that reduces the burden on the patient. In addition, by carrying out measurements using near infrared light that demonstrates different characteristics according to the composition of the adhered substances such as plaque within a blood vessel (light component contained in a measurement wavelength range from 780 nm to 2750 nm), analyses can be carried out that distinguish compositions such as plaque using an analyzing apparatus provided outside the blood vessel.

In addition, as indicated in the above-mentioned measurement examples, in the case of respectively illuminating the light components within the measurement wavelength range from 1400 nm to 1850 nm or from 1900 nm to 2700 nm, a characteristic intensity is indicated by light that has passed through or been reflected by plaque and the like adhered to a blood vessel wall. Thus, the compositions of substances adhered to a blood vessel wall at a measured portion can be analyzed more accurately by respectively calculating the second derivative of intensity information (such as the absorption spectrum) of light within the measurement wavelength range from 1400 nm to 1850 nm or from 1900 nm to 2700 nm.

Although the preceding has provided an explanation of the blood vessel wall analyzing apparatuses 1 and 2 according to the present embodiment, the blood vessel wall analyzing apparatus according to the present invention is not limited to the above-mentioned embodiment, but rather can be altered in various ways. For example, although the case of the measurement target of the blood vessel wall analyzing apparatus being an inner wall of a carotid artery was explained with respect to the previously described embodiment, the blood vessel targeted for measurement is not limited to a carotid artery.

In addition, a method of investigating plaque compositions was explained in the previously described measurement examples that consists of measuring the absorption spectrum within a specific wavelength range and carrying out second derivation on the result according to the wavelength to detect a peak originating in a specific component of plaque. However, it is not essential to determine the second derivative according to wavelength. In addition, a mode can also be employed in which, instead of measuring the absorption spectrum for near infrared light, the peak intensity of a light component that has passed through or been reflected by a measured portion is determined by illuminating one specific or a plurality of specific wavelengths of near infrared light onto the measured portion, and the ratio of components that constitutes plaque at the measured portion is measured based on this result.

REFERENCE SIGNS LIST

1, 2: blood vessel wall analyzing apparatus; 10: light source; 20: spectroscope; 30: light illuminating unit; 40: light receiving unit; and 50: analysis unit.

The invention claimed is:

1. A blood vessel wall analyzing method of analyzing a composition of a measured portion in a blood vessel by using a blood vessel wall analyzing apparatus comprising:

illuminating means for illuminating at least a light component in a measurement wavelength range of 780 nm to 2750 nm onto a measured portion within a blood vessel, the illuminating means including: a light illuminating unit installed at a first location at a first predetermined distance away from the blood vessel; and a light source that outputs the light component to be illuminated onto the measured portion through the light illuminating unit;

detecting means for detecting the light component from the measured portion, the detecting means including: a light entering unit installed at a second location, at a second predetermined distance away from the blood vessel, where the light component from the measured portion reaches; and a light receiving unit that detects the light component introduced through the light entering unit;

analyzing means for analyzing composition of the measured portion based on intensity information on the light component detected by the detecting means; and a spectroscope arranged in one of a light path between the light source and the light illuminating unit and a light path between the light entering unit and the light receiving unit, the spectroscope selecting, from light outputted from the light source, the light component within a detection wavelength range that is included in the measurement wavelength range and is narrower than the measurement wavelength range, the method comprising:

arranging: (1) one of the light illuminating unit and the light entering unit on epidermis of a neck, while the other is arranged in an esophagus; (2) both the light illuminating unit and the light entering unit on the epidermis of the neck while being separated from each other; or (3) both the light illuminating unit and the light entering unit in the esophagus while being separated from each other;

illuminating the light outputted from the light source onto the measured portion through the light illuminating unit;

selecting the light component with the detection wavelength range from the light outputted from the light source, by using the spectroscope;

detecting the light component that has selected by using the spectroscope and entered through the light entering unit from the measured portion; and generating analysis data for identifying the composition of the measured portion from intensity information on the detected light component.

2. The blood vessel wall analyzing method according to claim 1, wherein the detecting means detects the light component in the detection wavelength range which extends 15 nm on both short and long sides of a selected center wavelength, the selected center wavelength being each of one or more wavelengths selected from a wavelength group comprised of 1514, 1574, 1626, 1691, 1740, 1972, 2055, 2166, 2290, 2465 and 2544 nm, and wherein the analyzing means determines presence or absence of thrombi in the blood vessel.

3. The blood vessel wall analyzing method according to claim 1, wherein the detecting means detects the light component in the detection wavelength range which extends 15 nm on both short and long sides of a selected center wavelength, the selected center wavelength being each of one or more wavelengths selected from a wavelength group comprised of 1696, 1717, 2272 and 2629 nm, and wherein the analyzing means analyzes for determines presence or absence of an atheroma in the blood vessel for the analysis of compositions of the measured portion.

4. The blood vessel wall analyzing method according to claim 1, wherein the detecting means detects the light component in the detection wavelength range which extends 15 nm on both short and long sides of a selected center wavelength, the selected center wavelength being each of one or more wavelengths selected from a wavelength group comprised of 1690, 2294 and 2372 nm, and the analyzing means determines presence or absence of a lipid core in the blood vessel.

5. The blood vessel wall analyzing method according to claim 1, wherein a second derivative according to a wavelength of intensity information on the detected light component from the measured portion is calculated as analysis data within the detection wavelength range of 1400 nm to 1850 nm or 1900 nm to 2700 nm, and the composition of the measured portion is analyzed based on a result thereof.

6. The blood vessel wall analysis method according to claim 1, wherein image information relating to the composition of the measured portion is overlaid onto a two-dimensional tomographic image of the blood vessel, and a resulting two-dimensional image is displayed on a monitor.

\* \* \* \* \*